(12) United States Patent
Salgado

(10) Patent No.: US 9,863,858 B2
(45) Date of Patent: Jan. 9, 2018

(54) HEATING AND COOLING JACKET FOR TEST CELL

(71) Applicant: Brigido Salgado, Houston, TX (US)

(72) Inventor: Brigido Salgado, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 379 days.

(21) Appl. No.: 14/619,178

(22) Filed: Feb. 11, 2015

(65) Prior Publication Data
US 2015/0226649 A1 Aug. 13, 2015

Related U.S. Application Data

(60) Provisional application No. 61/939,048, filed on Feb. 12, 2014.

(51) Int. Cl.
*G01N 1/44* (2006.01)
*G01N 1/42* (2006.01)

(52) U.S. Cl.
CPC .............. *G01N 1/44* (2013.01); *G01N 1/42* (2013.01); *Y10T 29/4935* (2015.01)

(58) Field of Classification Search
CPC ........................................................ G01N 1/44
See application file for complete search history.

(56) References Cited

U.S. PATENT DOCUMENTS

| | | | | |
|---|---|---|---|---|
| 4,516,580 A | * | 5/1985 | Polanyi | A61B 5/145 210/321.63 |
| 4,521,225 A | * | 6/1985 | Jenkins | G01N 30/20 73/23.25 |
| 6,138,522 A | * | 10/2000 | Miyoshi | E21B 49/02 73/863.45 |
| 7,335,337 B1 | * | 2/2008 | Smith | B01L 3/0275 422/513 |
| 7,823,468 B2 | * | 11/2010 | Davison | G01N 30/20 137/625.16 |
| 2002/0178843 A1 | * | 12/2002 | Kriel | G01N 30/20 73/863.73 |
| 2014/0232218 A1 | * | 8/2014 | Takano | H02K 5/20 310/53 |

FOREIGN PATENT DOCUMENTS

| | | | |
|---|---|---|---|
| CN | 2013-C36862 | * | 11/2012 |
| CN | 203464809 | * | 3/2014 |

* cited by examiner

*Primary Examiner* — Robert R Raevis
(74) *Attorney, Agent, or Firm* — Keeling Law, LLC; Kenneth A. Keeling; Mark S. Solomon

(57) ABSTRACT

An exemplary embodiment of a jacket for heating and cooling a test cell generally includes an inner liner having an exterior channel along at least a portion of the liner exterior wall surface; an outer shell tightly fitted over the interior liner; openings provided in the outer shell, the openings proximate upper and lower ends or segments of the channel of the inner liner; and connectors provided on the outer shell openings for connection of fluid lines, thereby providing for fluid flow intermediate the upper and lower ends or segments of the channel of the inner liner. An exemplary embodiment of a method for producing the jacket generally includes providing the channel in the inner liner and providing an interference fit between the inner liner and the outer shell, whereby fluid communication there between, and a substantially fluidly impenetrable seal between the inner liner and the test cell, are provided.

4 Claims, 7 Drawing Sheets

HEATING AND COOLING JACKET FOR TEST CELL

CROSS-REFERENCE TO RELATED APPLICATIONS

This application claims the benefit of U.S. Provisional Application No. 61/939,048 filed on Feb. 12, 2014, which application is incorporated herein by reference as if reproduced in full below.

STATEMENT REGARDING FEDERALLY SPONSORED RESEARCH OR DEVELOPMENT

Not applicable.

FIELD OF THE DISCLOSURE

This invention relates generally to testing equipment used to measure properties of materials and chemical systems, and more specifically to a method of heating and cooling a test cell.

BACKGROUND

In the oil and gas industry, it is necessary to understand the material properties of compounds used during drilling and exploration and to determine how properties are affected by temperature, pressure, and time.

Test cells are variously used to determine properties of chemical systems, including, for example, drilling cement compositions for mechanical strength, gel strength, and other properties in relation to time, temperature and pressure variations relevant to drilling and cementing operations.

During common laboratory testing procedures, mixtures are prepared, inserted in a test cell, and subjected to temperature and pressure variations. As the test sample is sealed within a test cell container, heating and cooling of the test cell is conducted by applying cooling fluids and heat to the cell exterior.

Conventional test cells are generally constructed of stainless steel with upper caps and lower caps.

Conventional test cells may be heated with an electrical heating element included in a surrounding jacket. Conventional test cells may be heated or cooled by applying a liquid bath to the test cell. Conventional liquid baths can involve immersion of the test cell in an external container.

BRIEF SUMMARY OF THE DISCLOSURE

Embodiments of the present invention comprises a jacket for heating and cooling a test cell, comprising an inner liner having an exterior channel along a portion of the liner exterior external wall surface, an outer shell with interference fit to the interior liner for high heat transfer from heater to cell, openings provided in the outer shell, the openings proximate upper and lower ends or segments of the channel of the interior liner, connectors provided on the outer shell openings for connection of fluid lines, thereby providing for fluid flow intermediate the upper and lower ends or segments of the channel of the interior liner.

BRIEF DESCRIPTION OF THE DRAWINGS

For a more complete understanding of the exemplary embodiments, reference is now made to the following Detailed Description of Exemplary Embodiments of the Invention, taken in conjunction with the accompanying drawings, in which.

DESCRIPTION OF EXEMPLARY EMBODIMENTS OF THE INVENTION

Figure 1:
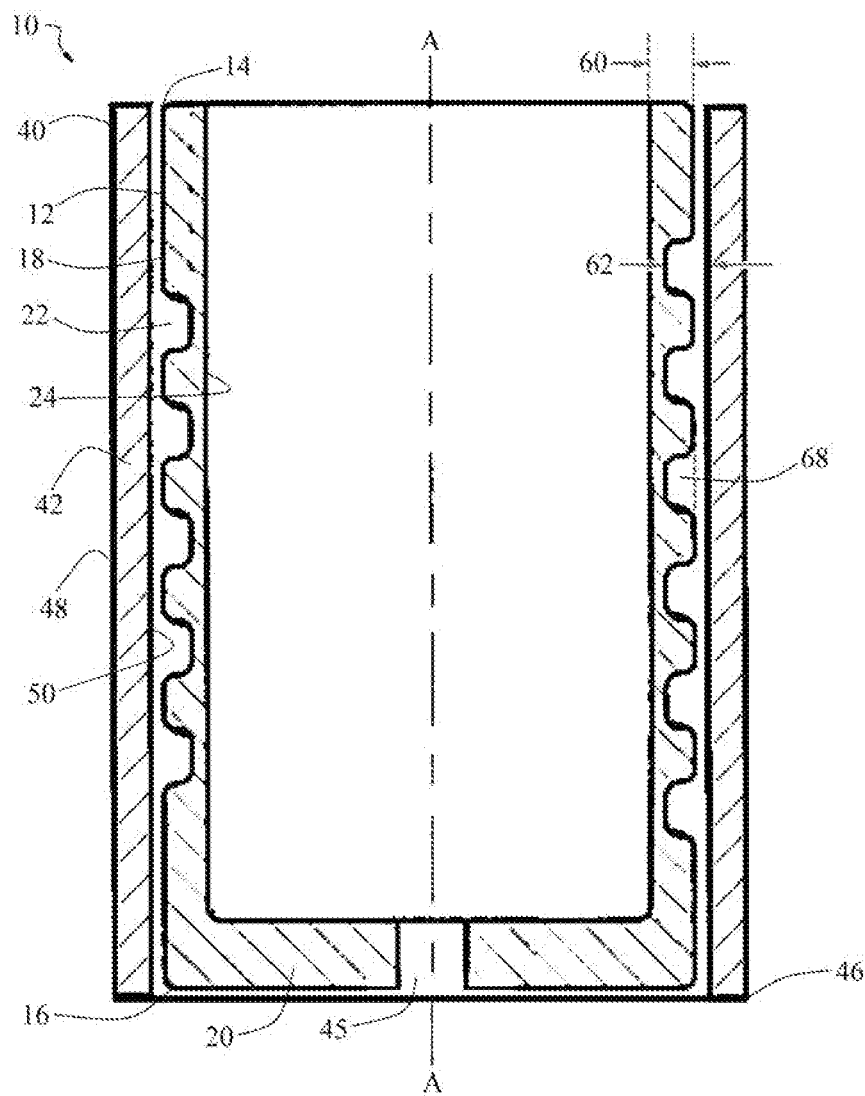
FIG. 1 depicts a cross-sectional view of a heating and cooling jacket of an embodiment of the present invention.

The exemplary embodiment is best understood by referring to the drawings, like numerals being used for like and corresponding parts of the various drawings.

The directions lower and upper as used in this specification are used for descriptive purposes only and it will be understood by one having skill in the art that different orientations are possible.

As used herein inner or inward means toward the axial center A-A of the heating and cooling jacket, and outer or outward means away from axial center A-A, unless the context indicates a contrary meaning.

Referring to FIG. 1, a cross-sectional view of a heating and cooling jacket 10 is depicted. Jacket 10 includes an inner liner 20 and an outer shell 40. Although inner liner 20 and outer shell 40 are depicted in FIG. 1 as substantially cylindrical in form, this representation is merely exemplary and other configurations are contemplated as being consistent with embodiments of the present invention.

Figure 2:
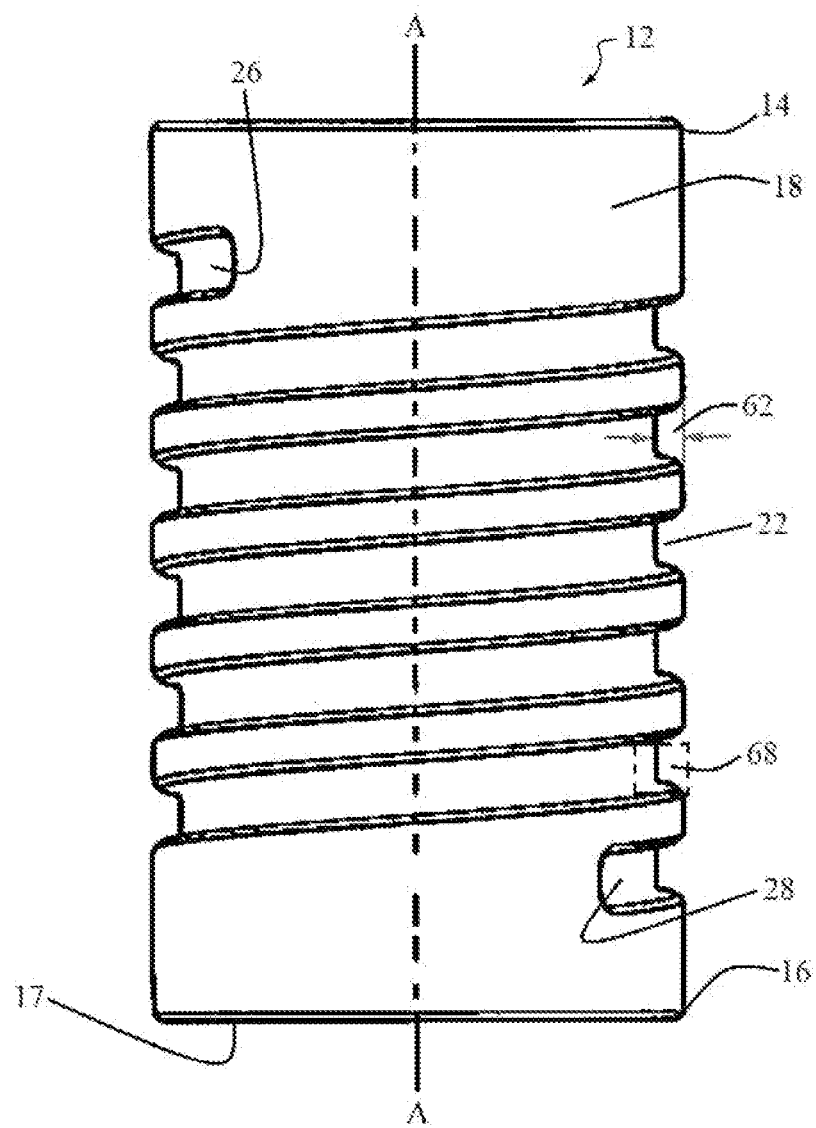
FIG. 2 depicts an external view of an inner liner of the heating and cooling jacket of an embodiment of the present invention.

Referring to FIGS. 1 and 2, inner liner 20 comprises a cylindrical liner wall 12 having an upper end 14 and a lower end 16. Wall 12 is attached at lower end 16 to a base 17. Inner liner 20 is open at its upper end 14. An opening 45 is provided in base 17. Opening 45 is substantially centered on axis A-A of cylindrical wall 12.

Wall 12 has an exterior surface 18 and an interior wall surface 24. A channel 22 is provided in exterior surface 18. The channel 22 may be provided in exterior surface 18 by mechanical machining or other suitable method as is known in the art. In one embodiment, channel 22 is substantially spiral with regard to wall 12, although other channel patterns may be employed. Spiral channel 22 extends inwardly of wall 12 from exterior wall surface 18. In one embodiment, an upper portion of spiral channel 22 (not separately labeled) comprises a channel upper end 26 and a lower portion of spiral channel 22 (not separately labeled) comprises a channel lower end 28. Upper end 26 of spiral channel 22 is proximate, but spaced from, upper end 14 of wall 12. Lower end 28 of spiral channel 22 is proximate, but spaced from, lower end 16 of wall 12. In this embodiment, spiral channel 22 extends continuously from upper end 26 to lower end 28. In an exemplary embodiment, spiral channel 22 is configured to provide multiple revolutions around wall 12 intermediate upper end 26 and lower end 28.

Figure 2A:
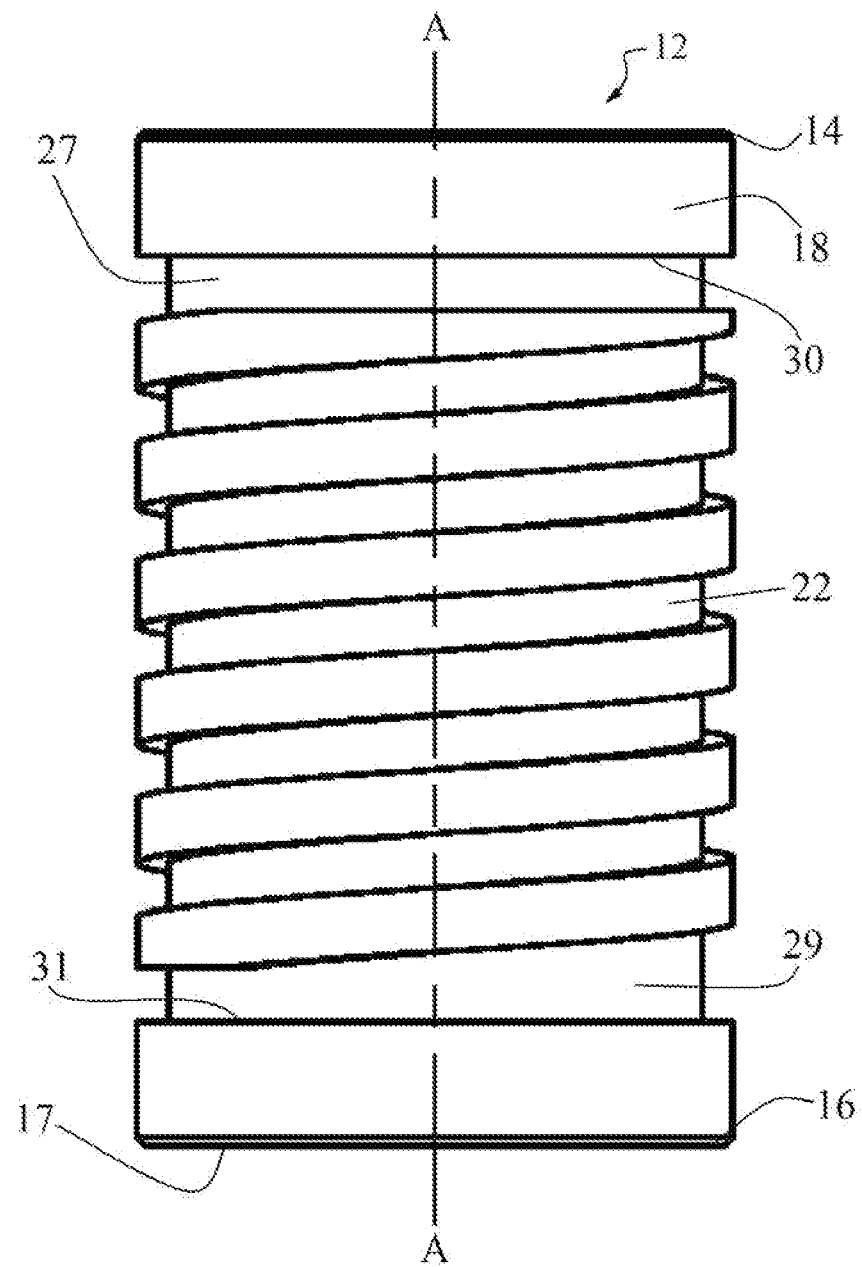
FIG. 2A depicts an external view of an inner liner of the heating and cooling jacket of an embodiment of the present invention.

In another embodiment of the present invention, as depicted in FIG. 2A, the upper portion of channel 22 does not comprise upper end 26, but rather comprises a channel upper segment 27 proximate, but spaced from, upper end 14 of wall 12, and the lower portion of channel 22 does not comprise lower end 28, but rather comprises a channel lower segment 29 proximate, but spaced from, lower end 16 of wall 12. Upper segment 27 and lower segment 29 each comprise a continuous, fluidly communicative loop circumferential to inner liner 20 within exterior surface 18. In one embodiment, an upper surface 30 of channel upper segment 27 and/or a lower surface 31 of channel lower segment 29 extend substantially perpendicular to axis A-A. In additional embodiments (not shown), channel 22 may comprise the combination of upper end 26 and lower channel segment 29, or the combination of lower end 28 and upper channel segment 27. In this embodiment, spiral channel 22 extends continuously from upper segment 27 to lower segment 29. In an exemplary embodiment, spiral channel 22 is configured to provide multiple revolutions around wall 12 intermediate upper segment 27 and lower segment 29.

Figure 3:
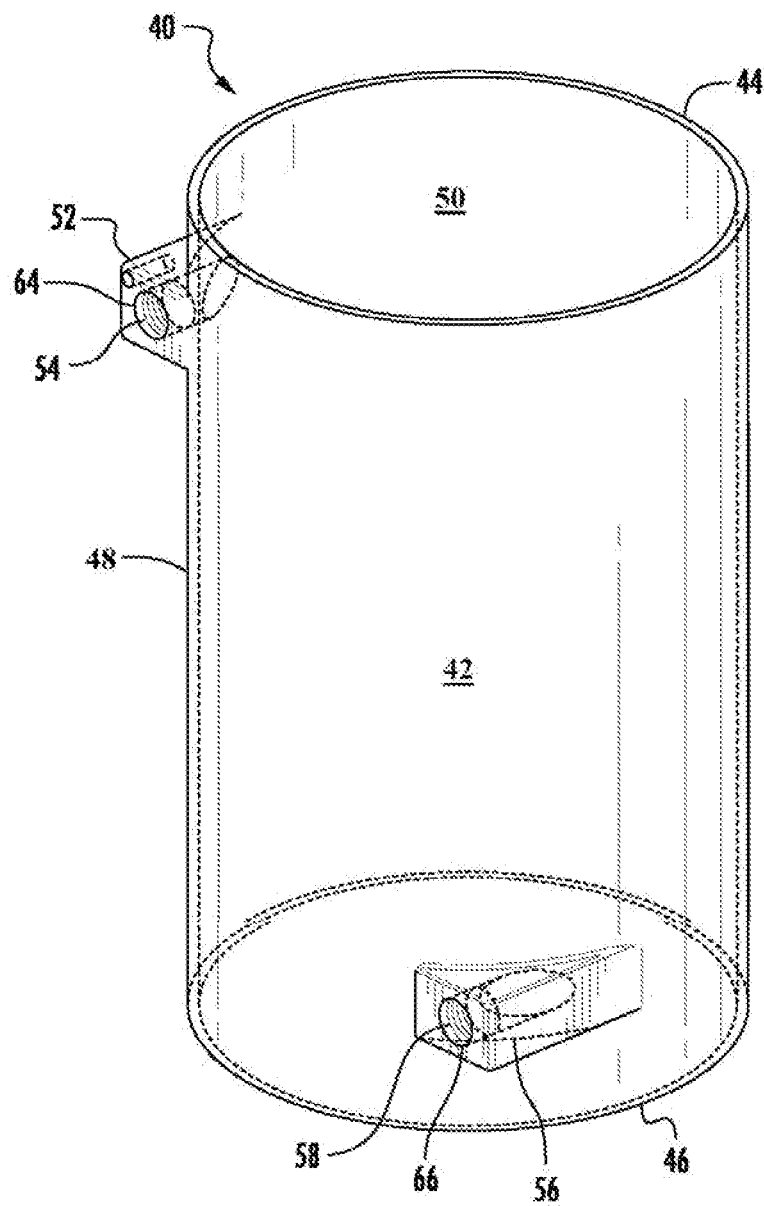
FIG. 3 depicts an external view of an outer shell of an embodiment of the present invention.

Referring to FIGS. 1 and 3, outer shell 40 comprises a cylindrical outer shell wall 42 having an upper end 44 and a lower end 46. In one embodiment, outer shell 40 is closed at lower end 46 and is open at upper end 44. In other embodiments, outer shell 40 may be at least partially open at upper end 44 and lower end 46. Outer shell wall 42 has an exterior surface 48 and an interior surface 50.

Referring to FIG. 3, an upper attachment nub 52 is provided on outer shell wall 42. An upper opening 54 extends thorough attachment nub 52 and outer shell wall 42. Upper attachment nub 52 and upper opening 54 are located proximate upper end 44, but spaced from upper end 44. A lower attachment nub 56 is provided on outer shell wall 42. A lower opening 58 extends through attachment nub 56 and wall 42. Lower attachment nub 56 and lower opening 58 are located proximate lower end 46, but spaced from lower end 46.

Outer shell 40 and inner liner 20 are constructed and shaped such that outer shell 40 may be slidably placed on inner liner 20 with interior surface 50 of outer shell wall 42 closely fitting exterior surface 18 of inner liner wall 12. Fit of outer shell 40 and inner liner 20 is sufficiently tight to provide water-impermeable sealing connection of surface 18 and surface 50. In one embodiment, to further assure provision of a sealed system, welding of at least a portion of inner liner 20 liner wall 12, proximate upper end 14 thereof, to at least a portion of outer shell 40 shell wall 42, proximate upper end 44 thereof, is performed.

In an exemplary embodiment, fit of outer shell 40 and inner liner 20 is an interference fit. In various embodiments, interference fit is accomplished by heating outer shell 40 prior to assembly, sliding outer shell 40 onto inner liner 20, and allowing outer shell 40 to cool after placement on inner liner 20; cooling inner liner 20 prior to assembly, sliding outer shell 40 onto inner liner 20, and allowing inner liner 20 to warm after placement within outer shell 40; and/or applying a force to bias outer shell 40 onto inner liner 20. To accomplish the interference fit, outer shell 40 is constructed at a nominal diameter of interior wall surface 50 and inner liner 20 is constructed with inner liner wall 12 exterior surface 18 at slightly larger nominal diameter than interior wall surface 50. In an exemplary embodiment, the diameter of interior wall surface 50 is 4.795 inches with a tolerance of +0.000 inches and −0.001 inches, and the diameter of exterior surface 18 is 4.797 inches with a tolerance of +0.001 inches and −0.001 inches.

In various embodiments, outer shell 40 and inner liner 20 are constructed and sized such that upper opening 54 of outer shell 40 is aligned with upper end 26 of channel 22, and such that lower opening 58 of outer shell 40 is aligned with lower end 28 of channel 22, upon attachment of outer shell 40 and inner liner 20. In additional embodiments, shell 40 and inner liner 20 are constructed and sized such that upper opening 54 of outer shell 40 is vertically aligned with upper channel segment 27, and such that lower opening 58 of outer shell 40 is vertically aligned with lower channel segment 29, upon attachment of outer shell 40 and inner liner 20.

In an exemplary embodiment outer shell 40 and inner liner 20 may be connected by sliding placement of outer shell 40 in relation to inner liner 20.

Figure 4:
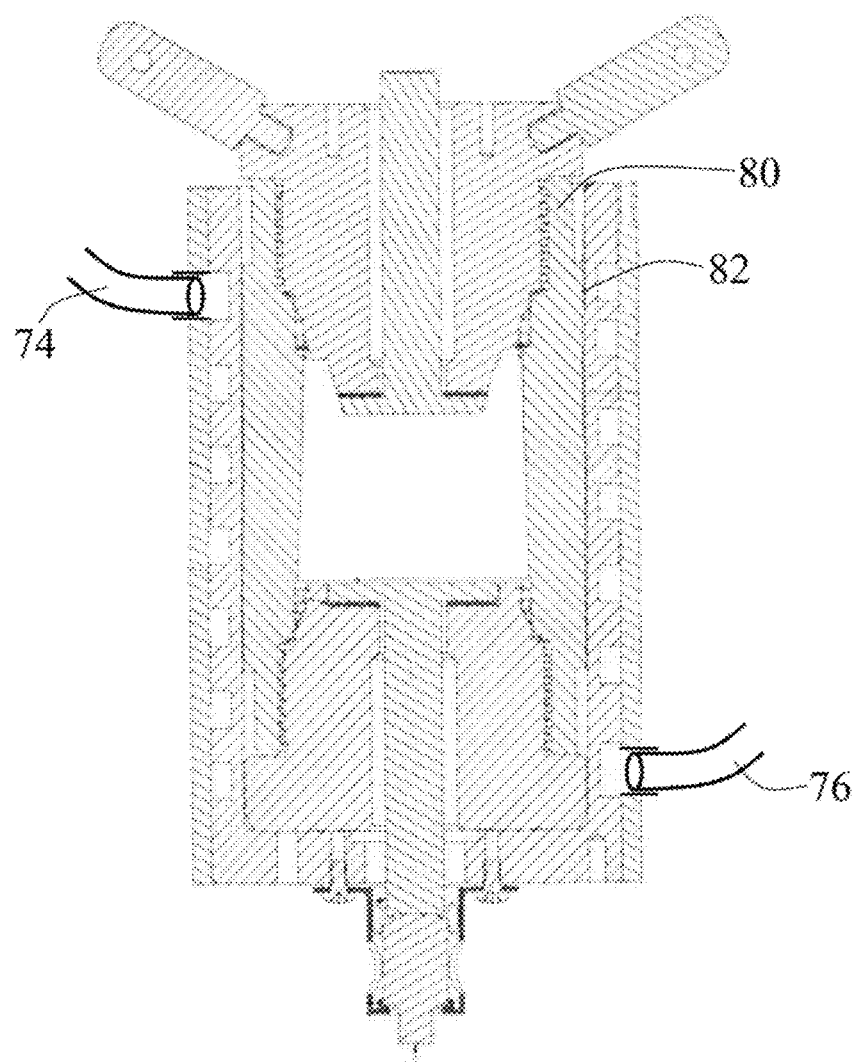
FIG. 4 depicts a cross-sectional view of a heating and cooling jacket of an embodiment of the present invention proximate a test cell.

Referring to FIGS. 3 and 4, upper opening 54 is provided with interior threading 64 to allow channeled connection of a flow line 74 to upper opening 54. Lower opening 58 is provided with interior threading 66 to allow channeled connection of a flow line 76 to lower opening 58. Such threaded connections are merely exemplary, and other connection mechanisms, as are known in the art, may be employed. In various embodiments, flow lines 74 and 76 are adapted to allow the use of heating and/or cooling fluids.

FIG. 4 depicts a cross-sectional view of a heating and cooling jacket 10 of the present invention in relation to an exemplary test cell 80. Inner liner 20 is constructed to closely fit exterior surface 82 of test cell 80.

In an exemplary embodiment, inner liner 20 comprises one or more materials having relatively high heat transfer characteristics, such as aluminum, steel, or brass. In an exemplary embodiment, outer shell 40 comprises one or more materials having relatively high heat transfer characteristics, such as aluminum, steel, or brass.

Figure 5:
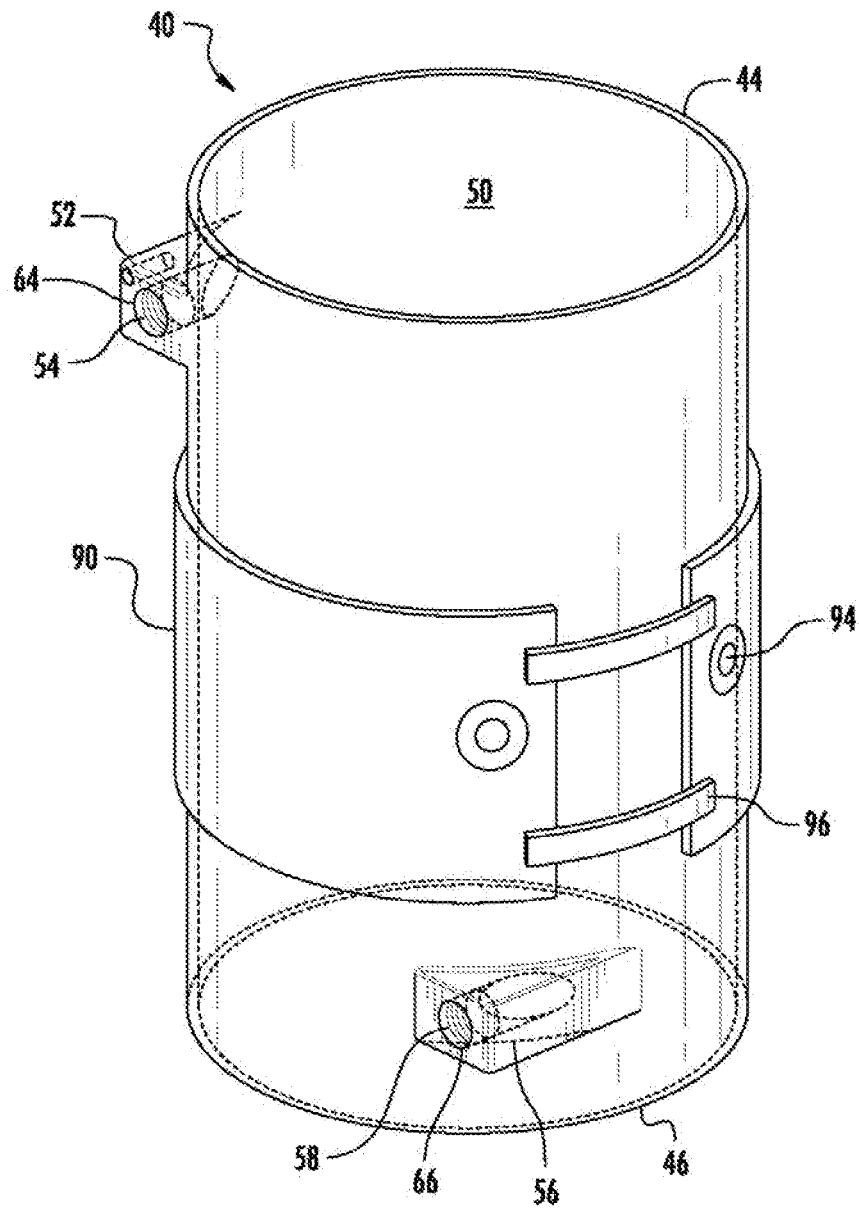
FIG. 5 depicts an external view of the heating and cooling jacket of an embodiment of the present invention with attached heating element.

Referring to FIG. 5, an alternative exemplary embodiment of the present invention is depicted. In the embodiment of FIG. 5, a heating element 90 is positioned on jacket 10. In the embodiment depicted, heating element 90 is electrically powered and includes electrical contacts 94 and connectors 96. In the embodiment of FIG. 5, heating may be supplied by heating element 92, either alone or in conjunction with heated liquid circulated through channel 22. In the embodiment of FIG. 5, a heating or cooling fluid may be circulated through channel 22 independent of heating element 90. Heating elements 90 are known in the art as a means of heating a test cell such as exemplary test cell 80.

In an exemplary embodiment, wall 12 is constructed with a wall thickness 60 in the range of 0.3 inches to 0.5 inches. In one embodiment, a depth 62 of channel 22 is equal to or greater than ½ of wall thickness 60.

In an exemplary embodiment, cross-sectional area 68 of channel 22 is constructed to be greater than the cross-sectional area of upper opening 54 (not labeled in Figures), and cross-sectional area 68 of channel 22 is constructed to be greater than the cross-sectional area of lower opening 58 (not labeled in Figures). Accordingly, flow within channel 22 is not restricted in relation to either of upper opening 54 and lower opening 58.

Operation

In operation, using various embodiments of the jacket of the present invention, a sample (not shown) is provided in a test cell 80. Test cell 80 is slidably inserted into inner liner 20, with outer surface 82 of test cell 80 proximate inner surface 24 of inner liner 20.

To heat test cell 80, hot fluid (not shown) is provided from a fluid source (not shown) and circulated through flow line 74, through channel 22, and returned through flow line 76. In an alternative embodiment, a heating element 92 may be attached to exterior surface 48 of outer shell 40. Heat may be applied to test cell 80 through heating element 92 independently of fluid flow through channel 22.

To cool test cell 80, a fluid (not shown) at a lower temperature than the temperature of test cell 80 is provided from a fluid source (not shown) through flow line 74, allowed to flow through channel 22, and returned through flow line 76.

Various monitors and controls, known in the art, may be utilized to control liquid temperature and liquid flow.

In essence, flow of liquid through channel 22 provides effective heat transfer between the liquid and inner liner 20, with corresponding heat transfer between inner liner 20 and test cell 80.

Method

Figure 6:
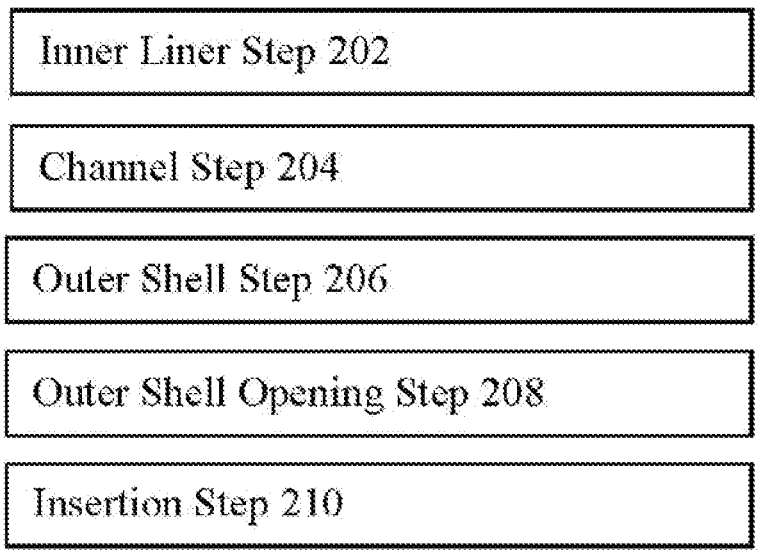
FIG. 6 depicts a method of constructing a heating and cooling jacket of an embodiment of the present invention.

Referring to FIG. 6, a method 200 of constructing a heating and cooling jacket 10 of embodiments of the present invention comprises:

An inner liner step 202 of providing a cylindrical inner liner 20 with a cylindrical liner wall 12 and a base 17, said base 17 having a center opening 45.

A channel step 204 of cutting a channel 22 in wall 12, said channel 22 extending spirally and circumferentially in wall 12, and extending inwardly from exterior surface 18 of wall 12, such channel having an upper end 26 and a lower end 28, with upper end 26 spaced from upper end 14 of wall 12, and lower end 28 spaced from lower end 16 of wall 12. In an alternative embodiment, channel 22 is cut to comprise an upper channel segment 27 and a lower channel segment 29, with upper channel segment 27 spaced from upper end 14 of wall 12, and lower channel segment 29 spaced from lower end 16 of wall 12.

An outer shell step 206 of providing a cylindrical outer shell 40 for interference fit with exterior surface 18 of wall 12.

An outer shell opening step 208 of providing an outer shell upper opening 54 and a outer shell lower opening 58, with opening 54 sized and constructed to fluidly engage channel 22 upper end 26, and opening 58 sized and constructed to fluidly engage channel 22 lower end 28, and with attachment nub 52 at shell opening 54 and attachment nub 56 at shell opening 58.

An insertion step 210 of inserting inner liner 20 in shell 40, with opening 54 aligned with channel end 26 or upper channel segment 27, and opening 58 aligned with channel end 28 or lower channel segment 29.

In an exemplary embodiment, insertion step 210 comprises an interference fit of shell 40 on liner 20, such interference fit accomplished by relative thermal expansion of shell 40, thermal contraction of liner 20, and/or applying force to bias shell 40 tightly onto liner 20.

Various embodiments will be understood from the foregoing description, and it will be apparent that, although embodiments have been described in detail, various changes, substitutions, and alterations may be made in the manner, procedure and/or details thereof without departing from the spirit and scope or sacrificing any of its material advantages, the forms hereinbefore described being merely exemplary embodiments thereof.

I claim:

1. An apparatus for heating and cooling a test cell, comprising:
    a substantially cylindrical inner liner adapted to accommodate at least a portion of said test cell there within, wherein:
        said inner liner comprises a substantially cylindrical exterior wall surface;
        said exterior wall surface comprises a spirally disposed channel formed therein: and
        said channel comprises a channel upper portion and a channel lower portion;
    an outer shell adapted to accommodate at least a portion of said inner liner there within, wherein:
        said outer shell comprises:
            a substantially cylindrical interior wall surface;
            an upper opening in said interior wall surface that is adapted to be fluidly connectable to a component external to said outer shell; and
            a lower opening in said interior wall surface that is adapted to be fluidly connectable to a component external to said outer shell; and
        said outer shell is adapted to accommodate said inner liner there within, whereby:
            a substantially fluidly impenetrable seal is formed between said exterior wall surface and said interior wall surface;
            said upper opening is aligned in fluid communication with said channel upper portion; and
            said lower opening is aligned in fluid communication with said channel lower portion; and
        a heating element is disposed around said outer shell.

2. The apparatus of claim 1, wherein:
    said channel upper portion comprises a component selected from the group consisting of:
        a channel upper end; and
        a channel upper segment; and
    said channel lower portion comprises a component selected from the group consisting of:
        a channel lower end; and
    a channel lower segment.

3. The apparatus of claim 1, wherein said outer shell is adapted to allow said inner liner to be inserted there within by one or more modes of action selected from the group consisting of:
    heating said outer shell;
    cooling said inner liner; and
    applying force to bias said outer shell onto said inner liner.

4. The apparatus of claim 1, wherein at least one of said inner liner and said outer shell comprises a material having relatively high heat transfer characteristics.

* * * * *